US006351660B1

(12) United States Patent
Burke et al.

(10) Patent No.: US 6,351,660 B1
(45) Date of Patent: Feb. 26, 2002

(54) ENHANCED VISUALIZATION OF IN-VIVO BREAST BIOPSY LOCATION FOR MEDICAL DOCUMENTATION

(75) Inventors: Thomas M. Burke, Bothell, WA (US); David T. Carrott, Bristow, VA (US)

(73) Assignee: Litton Systems, Inc., Agoura Hills, CA (US)

( * ) Notice: Subject to any disclaimer, the term of this patent is extended or adjusted under 35 U.S.C. 154(b) by 0 days.

(21) Appl. No.: 09/551,456

(22) Filed: Apr. 18, 2000

(51) Int. Cl.[7] ............................................... A61M 5/65
(52) U.S. Cl. ...................... 600/425; 600/437; 600/443; 600/444; 382/128; 359/32; 359/33; 378/98.11; 378/12
(58) Field of Search ................................ 382/128, 130, 382/131, 132; 359/32, 33; 378/98.11, 12; 600/407, 425, 437, 443, 444; 128/921, 922, 923

(56) References Cited

U.S. PATENT DOCUMENTS

| 5,209,232 A | 5/1993 | Levene | 128/653.1 |
| 5,803,912 A | 9/1998 | Siczek et al. | 600/407 |
| 5,820,552 A | 10/1998 | Crosby et al. | 600/407 |
| 5,833,627 A | 11/1998 | Shmulewitz et al. | 600/562 |
| 5,868,673 A | * 2/1999 | Vesely | 600/407 |
| 5,961,457 A | * 10/1999 | Raylman et al. | 600/436 |
| 6,022,325 A | * 2/2000 | Siczek et al. | 600/568 |

* cited by examiner

Primary Examiner—Marvin M. Lateef
Assistant Examiner—Jeoyuh Lin
(74) Attorney, Agent, or Firm—Koppel & Jacobs

(57) ABSTRACT

An image processing system and method visually documents and displays the in-vivo location from which a biopsy specimen was extracted, by processing pre-biopsy and post-biopsy images. A composite image is created which visually emphasizes differences between the pre-biopsy and post-biopsy images. Preferably three-dimensional, digitized images, displayable in various projections, are stored for archival purposes on computer readable media. An image processor preferably exploits an optical correlator to register the pre-biopsy and post-biopsy images accurately. The images are then compared, voxel-by-voxel, to detect differences between pre-biopsy and post-biopsy images. The composite image is displayed with synthetic colors, synthetic icons, or other visual clues to emphasize probable in-vivo biopsy locations.

23 Claims, 9 Drawing Sheets

ENHANCED VISUALIZATION OF IN-VIVO BREAST BIOPSY LOCATION FOR MEDICAL DOCUMENTATION

BACKGROUND OF THE INVENTION

1. Field of the Invention

The invention relates generally to ultrasonic and radiographic medical imaging, and particularly to three-dimensional, ultrasonic mammography and breast tissue biopsy techniques.

2. Description of the Related Art

Currently, the standard of care for managing breast disease includes breast biopsy to definitively diagnose suspicious lesions. Recently, stereotactically guided breast biopsy techniques have been introduced which allow more accurate guidance of the biopsy instruments, to improve the accuracy of the tissue sampling. It is scientifically, medically, and legally desirable to provide permanent, archivable imagery which documents the tissue sampling, recording precisely the location of each tissue specimen in relation to a suspected lesion and other pathological structures. This task is particularly difficult because the tissue and the lesion are three-dimensional structures, while most imagery used for guidance is two-dimensional.

A traditional method of documenting sterotactic biopsies is to take stereotactic images after a needle has been inserted into a lesion but before the tissue sample is actually taken. If microcalcifications are present, the standard of care specifies that X-ray images must be taken of the tissue samples and that the number of microcalcifications present in these samples must equal the number counted in the original screening mammograms. A free hand biopsy usually includes taking a single X-ray image showing the location of the needle and the lesion. Before and after images are not generally provided.

Interpretation of biopsy-documenting X-ray images is complicated in part because the lesion sampled is a three-dimensional volume, while the image is a projection onto a two-dimensional plane or planes. In addition, the breast may move slightly or be slightly deformed between the image and the biopsy. Another drawback is the need for multiple X-rays of the tissue, which expose the patient to ionizing radiation. Such methods are also inherently inconvenient because the mammograms are not typically immediately available. The patient must wait until the verifying mammograms are produced; and if a post-biopsy mammogram shows that the intended target was missed, additional needle insertions will be required.

Some biopsy guidance methods use ultrasound as an imaging medium to guide a biopsy instrument during insertion. For example, U.S. Pat. No. 5,833,627 to Shmulewitz (1998) describes a method and apparatus for guiding a biopsy needle or the cannula of a biopsy device while inserting it into a tissue mass. His apparatus uses ultrasonography in real time to aid in aligning the biopsy device with the ultrasound image. Similarly, U.S. Pat. No. 5,820,552 to Crosby et al. (1998) describes another apparatus and method which can be used to guide the trajectory of a breast biopsy instrument by employing real time imaging, typically ultrasonography, to enhance accuracy and ease of positioning the instrument.

Ultrasonography is limited in its ability to image certain types of tissues, however, which limits the above described methods. The lower resolution of ultrasonic imaging (compared to x-ray) makes it difficult or impossible to identify fine features, such as hard micro-calcifications in breast tissue, which would be more visible in an x-ray. Imaging of small calcifications is particularly important because such calcifications play an crucial role in the detection of breast cancer. They are frequently the only detectable early sign of breast cancer. Micro-calcifications are typically categorized as either benign, probably benign, or suggestive of malignancy, based on a number of factors including size, shape, and distribution. While some benign calcifications cannot be distinguished from those associated with malignancy, many can be so distinguished by their patterns and distribution. Often these calcifications mark a site which is sufficiently suspicious to merit biopsy.

X-ray mammography is superior in its ability to image microcalcifications, and has been used to guide a biopsy. For example, an x-ray guidance technique is described in U.S. Pat. No. 5,209,232 to Levene and Hadarom (1993). That Patent discloses a system using digital x-ray fluoroscopic imagery, taken from multiple angles, to guide a biopsy needle to its target. This method suffers from at least one obvious drawback: digital x-ray fluoroscopic equipment adequate for that method is quite expensive and bulky. Furthermore, fluoroscopic images are generally considered non-diagnostic (they can direct a biopsy, but lack sufficient resolution for screening or to see microcalcifications).

X-ray mammography also has other shortcomings. This technique provides detailed image information about well differentiated materials (such as bone or other calcified tissue), but it performs poorly at discriminating between soft tissues with subtle differences in density and structure. Some women have mammographically dense breasts, as compared to more fatty breasts. Images from such breasts are generally not clinically useful. The use of x-rays for examination also necessarily results in the exposure of the patient to ionizing radiation, which has well know associated risks. The technique is also limited in that it projects three-dimensional structure onto a two-dimensional plane, and thus does not directly capture the elevation or depth (position in the direction of radiation propagation) of features of interest.

Other biopsy positioning methods and apparatus are known, for example U.S. Pat. No. 5,803,912 to Siczek et al. (1998) and U.S. Pat. No. 5,868,673 to Vesely (1999) ("A System for Carrying Out Surgery, Biopsy and Ablation of a Tumor or Other Physical Anomaly"). Vesely's method requires implantation of an ultrasonic reference transducer, which must be positioned based on at least two mammograms. This method is apparently best suited to tumors of macroscopic size rather than small microcalcifications (or clusters thereof).

Although the aforementioned methods and apparatus aid in obtaining proper biopsy specimens (by guiding the instrument during the biopsy), none of these prior approaches explicitly provides affordable, archivable, easily viewed post-biopsy imagery for easy verification that the biopsy was taken from the precise intended volume.

SUMMARY OF THE INVENTION

An image processing system and method visually documents and displays the in-vivo location from which a biopsy specimen was extracted, by processing pre-biopsy and post-biopsy images. A composite image is created which visually emphasizes differences between the pre-biopsy and post-biopsy images. Preferably three-dimensional, digitized images, displayable in various projections, are stored for archival purposes on computer readable media.

To properly relate the pre-biopsy and post-biopsy images, an image processor preferably exploits an optical correlator to register the images accurately, by finding a transformation which produces a pre-determined degree of correlation between the images, then adjusting one image accordingly. The images are then compared, volume element by volume element ("voxel by voxel"), to detect differences between pre-biopsy and post-biopsy images. The composite image is displayed with synthetic colors, synthetic icons, or other visual clues to emphasize probable in-vivo biopsy locations.

BRIEF DESCRIPTION OF THE DRAWINGS

FIG. 2b is a flow diagram showing the continuation of the method of FIG. 2a;

DETAILED DESCRIPTION OF THE INVENTION

Figure 1:
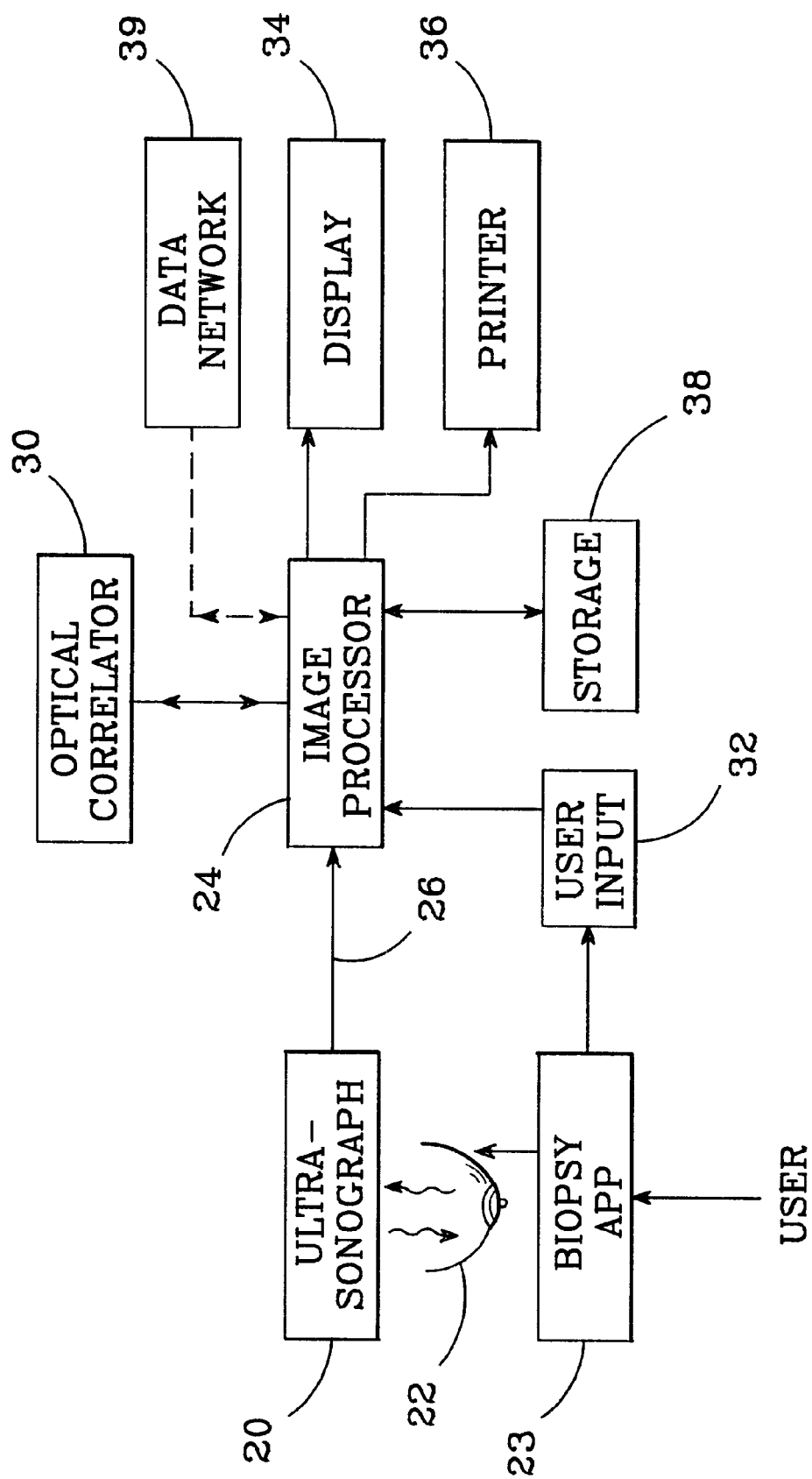
FIG. 1 is a system level block diagram of an apparatus in accordance with the invention.

FIG. 1 shows an apparatus in accordance with the invention and suitable for practicing the method of the invention for biopsy verification. An ultrasonographic imaging system 20 (or its equivalent) images a patient's breast 22, which is suitably positioned to permit access by a biopsy apparatus 23. The imaging system 20 provides digital image data to an image processor 24 via an input channel 26. An optical correlator 30 is preferably interfaced with the image processor 24 and controlled by the image processor 24 to provide high-speed image processing (correlations) of pre-processed image data. A user input device 32 (typically a keyboard and/or graphical pointing device such as a mouse) is interfaced to the image processor 24 to allow user control of the image processor 24. Graphic output is displayed by the image processor 24 on a display 34, which is preferably a color-capable video display. A printer 36 is preferably also interfaced with image processor 24 to produce "hard copy" printouts which record the biopsy, most preferably with multi-color, high resolution graphics. A storage device 38 such as a CD-ROM writer, digital tape storage, DVD, or similar digital storage device should preferably be also interfaced with the image processor 24 to record and store the biopsy results in a digital data format, for archiving. Optionally, the entire apparatus could be also interfaced to a data network 39 to allow the exchange of data with distant users, or to access other sources of image data.

The image processor 24 is preferably a 64 bit workstation such as the Silicon Graphics O2, although less powerful processors could be used at the expense of speed or resolution. The ultrasonographic imaging system 20 should preferably be capable of sweep scanning, to provide the multiple slices of imagery for assembly into a three-dimensional data set. Either a dedicated processor integral with the ultrasonographic imaging system 20 could provide such assembly, or it could alternatively be performed by the image processor 24.

Figure 2A:
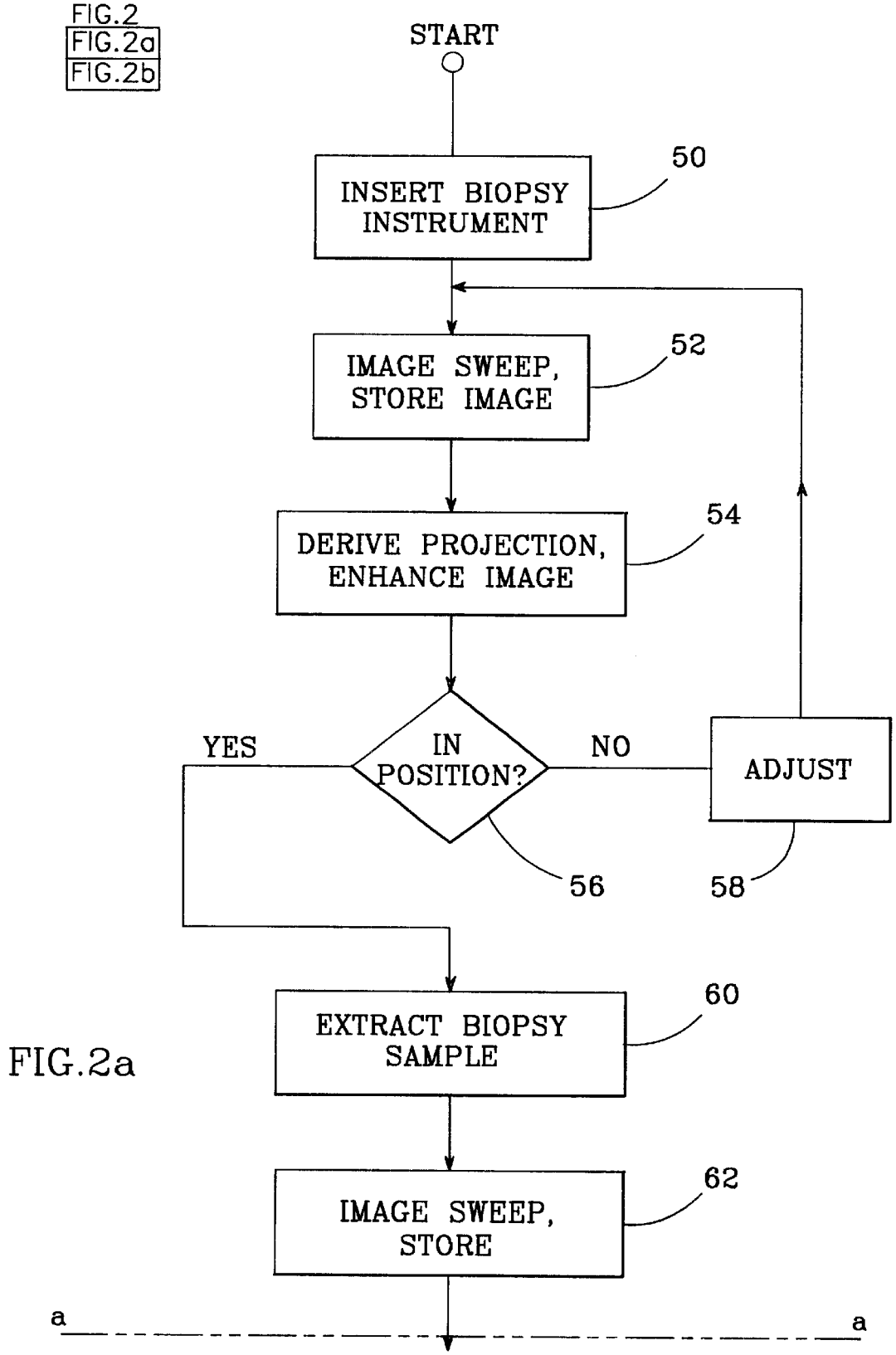
FIG. 2a is a flow diagram of a method for documenting the location from which a biopsy specimen was taken, in accordance with the invention.
Figure 2B:
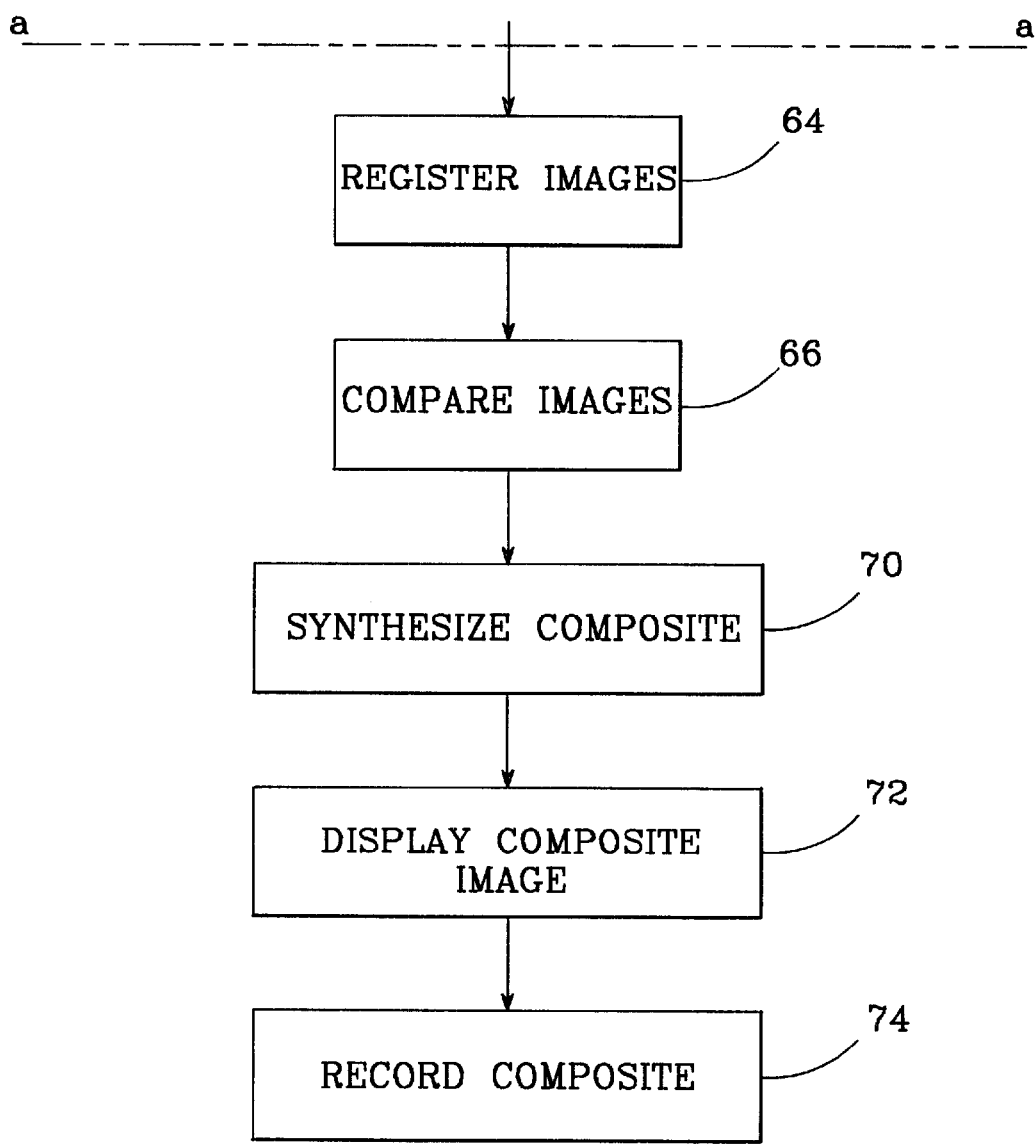

FIGS. 2a and 2b show a summary level flow chart of a method used in accordance with the invention to verify and document biopsies. Preliminarily, before applying the method of the figures, the breast should preferably scanned by ultrasound and/or the best available historical images should be consulted, to determine the best estimate of the suspected tumor's position, and the most appropriate entry point and angle for a biopsy. Based on the operator's preliminary estimate of position and angle, in step 50 a biopsy instrument is inserted into the breast with position. Next (step 52) a three-dimensional image sweep is taken, preferably by sweeping an ultrasonic imaging head linearly across the breast, thereby obtaining a plurality of image slices, which can be assembled into a three-dimensional image. The resulting image is stored (also in step 52). The image processor 24 then is commanded by the operator to manipulate the three-dimensional image to derive a useful projection or projections to aid in guiding the instrument to the desired target (step 54). Various projections could be used, including perspectives or simple plane and elevation stereotactic projections (with or without magnification), according to operator preference. Thresholding, edge detection or other known image enhancement techniques could optionally be applied as part of this step.

Next, the operator makes a preliminary decision as to whether the positioning of the instrument is proper for obtaining a sample of the biopsy target (decision box 56). If not, the position is further adjusted (step 58) and the three-dimensional image sweep is repeated (step 52). Ultrasonography is advantageous in that the image is obtained quickly, so the scanning can be done in real time and nearly continuously. Once the instrument is shown to be in proper position, as desired by the operator, the biopsy sample is extracted (step 60). If the biopsy instrument is a biopsy "gun", then a spring loaded instrument typically retracts quickly, while extracting a core of tissue. If, on the other hand, a vacuum assisted device is used, activation consists of applying the vacuum to a needle-like probe, and sucking small areas of tissue through the probe into a sampling vessel.

Referring not to FIG. 2b, after the sample is taken (step 60 of FIG. 2a), another three-dimensional image sweep is performed and stored (step 62). The image processor then registers (step 64) the pre-biopsy image (stored in step 52) and the post-biopsy image (stored in step 62), preferably by using an optical correlator to find an acceptable coordinate transformation, in the manner explained in detail below, in connection with FIGS. 5a, 5b and 6. Due to the biopsy tissue extraction, the pre-biopsy and post biopsy images will differ slightly. The properly registered pre-biopsy and post biopsy images are then compared, preferably voxel-by-voxel at corresponding voxel locations (step 66). (a "voxel" is a unit of graphic information that defines a small volume element in three-dimensional space. It is the three-dimensional analog of a "pixel" which defines an area element in two-dimensional space.) For example, normalized before and after images can be substractively compared, voxel by voxel, to obtain a three-dimensional difference image which represents the differences between the before and after images.

Several differences are detectable by the above described comparison. First, the path taken by the biopsy needle will generally appear as a faint, low density trail in the post biopsy image. Second, after removal of biopsy specimens, the site of tissue removal is detectable as a void or region of low density. Both of these changes are easily detected by comparing the three-dimensional images voxel-by-voxel, provided that the images have been registered so that corresponding voxels are compared.

After comparison of the pre-biopsy and post-biopsy images, an enhanced composite image (preferably three dimensional) is synthesized (step 70) which emphasizes the image differences. The enhanced combination image, for example, can be color-coded to emphasize the regions where differences were detected. For example, image data which was present in the pre-biopsy but absent after can be coded as pink, with intensity dependent on density. Thus, the biopsied tissue (and the biopsy needle or instrument) can be highlighted (in pink, for example). Image information which is present in the post-biopsy but not previously can be highlighted in a different color. Image information common to both images can be shown in grey scale. Thus a composite image is synthesized which includes information from both pre-biopsy and post-biopsy scans, while visually emphasizing differences. This is useful as a way to highlight areas which may have been obscured (for example, shadowed by the biopsy instrument or an overlying tumor) in pre-biopsy imagery.

The composite image is then displayed for operator inspection (step 72) and recorded (step 74) for archival purposes, preferably on a high-density, long persistence medium such as magnetic tape memory or writable CD-ROM. Preferably a three-dimensional volume image is stored, but to save storage space, operator selected projections can be derived (by the image processor 24 under control from the operator) and stored as two-dimensional imagery. Three dimensional imagery is preferred, despite its greater storage demands, because it can be more easily compared with other images (either previous history or subsequent development). The three-dimensional imagery can be digitally manipulated by rotation, scaling, translation then projected to provide comparison with any view; two dimensional imagery does not provide sufficient information to carry out the aforementioned manipulations without loss of information or introduction of ambiguities in the resulting image. The location of the biopsy in the image should preferably be tagged by association with identifying data, to cross-link to the actual tissue sample specimen number for future reference.

As an alternative or in addition to highlighting the differences between pre-biopsy and post-biopsy images, a three-dimensional icon representing an idealized geometric shape, approximating the actual biopsy sample, can be inserted digitally (by the image processor 24) into the three-dimensional imagery at the location where the tissue was extracted (as determined by before and after comparison step 66, above). For example, certain biopsy instruments are designed to extract a cylindrical core. A small cylindrical icon can be digitally synthesized and inserted into the combined image at the determined location from which the sample tissue was extracted.

The method may be repeated to sample and record multiple biopsies, with or without removal of the biopsy instrument (in the case of vacuum assisted biopsy devices) Either one or multiple combined images can be stored for archival and to document the biopsy procedure. The multiple individual biopsy sites are preferably tagged by association with corresponding identifying data codes, to allow cross-linking actual tissue specimens to respective locations of extraction.

Besides color coding and icon placement, other types of visual emphasis can be employed to highlight image differences between pre-biopsy and post-biopsy. For example, data points (image regions) which show a pre-determined degree of change can be displayed with flicker or blinking for emphasis, while other image areas showing less change remain static on the display. Many variations and combinations of visual display strategies are possible.

The accuracy and precision of the above described procedure depends in part upon the accuracy with which the pre and post-biopsy imagery are registered (in step 64 of FIG. 2a) before comparison. Slight movement or deformation of the breast tissue or the scanning apparatus is to be expected between the pre-biopsy and post-biopsy scans (steps 52 and 62 of FIG. 2a). The movement may include translation, rotation about any axis, or slight compression or expansion (in addition to tissue removal). To adequately register the images in step 64, therefore, a computationally practical and fast method of registration is preferred. A preferred method of registration takes advantage of the specific computational abilities of an optical correlator (discussed in detail below in connection with FIG. 9). This preferred method (suitable for use in step 64 of FIG. 2a) is best described with reference to an example of a particular coordinate system, to aid in visualization.

Figure 3:
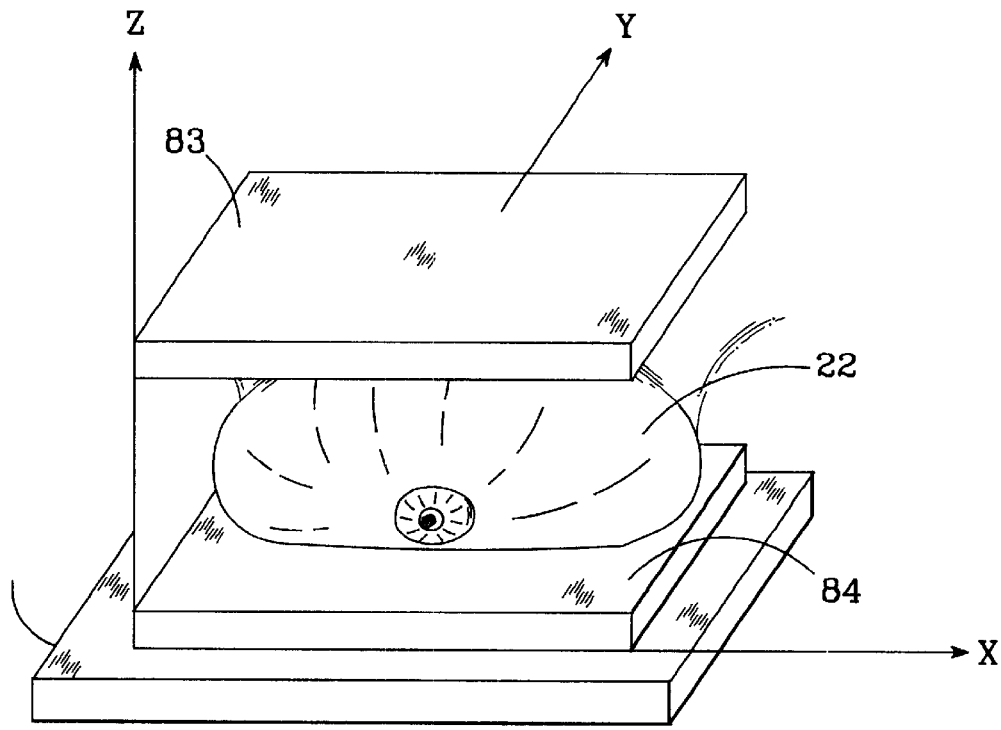
FIG. 3 is a perspective view of one geometric arrangement which can be used to obtain ultrasonographic imagery of a human breast for use by the invention.

FIG. 3 shows how a sonographic or radiographic breast image might be oriented with respect to a particular useful coordinate system. The system is conveniently illustrated in a Cartesian, rectilinear coordinate system having linear, perpendicular axes x, y and z, but the invention is not limited to such a coordinate system. The patient's breast 22 is scanned with ultrasound by the ultrasonic imaging system 20 (omitted for clarity, but shown in FIG. 1). With a patient preferably sitting facing the imaging system, the patient's breast 82 is preferably slightly compressed between pressure plates 83 (upper) and 84 (lower) in a manner that makes maximal use of prior information (such as x-ray images). In positioning the breast between the pressure plates, edges of the plates will contact the patient's chest above and below the breast. Because of slight movement between image acquisitions, the patient's breast in the imaging system, the axes of the post-biopsy imagery do not in the general case exactly correspond with the x, y and z axes of the pre-biopsy image, but may differ by a coordinate transformation: for example, they may differ by translation in the x, y or z directions, and by rotation about any axis. Rotation about the z axis is especially likely.

Figure 4:
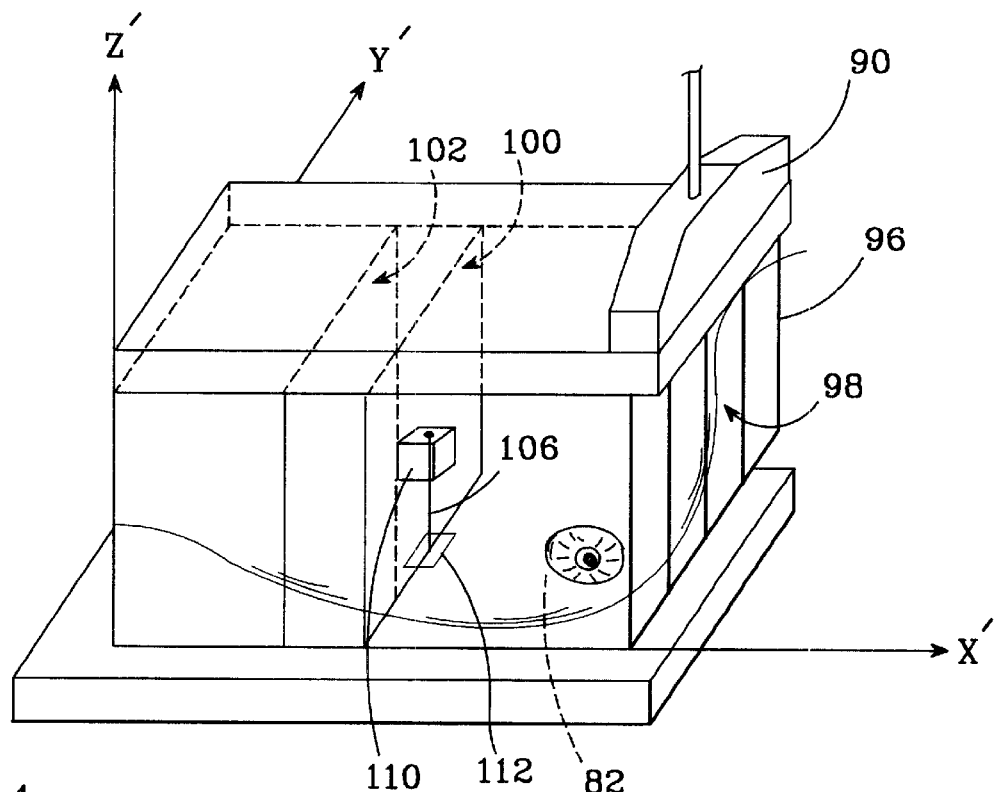
FIG. 4 is a perspective view of the arrangement of FIG. 3, showing further details of a scanning scheme for obtaining three-dimensional image data from a human breast.

With the breast 82 in position, ultrasonic scanning is preferably performed in planes (or surfaces), which will in general be non-parallel to that of the Y-Z plane in FIG. 3. FIG. 4 shows a typical geometry in which the scanhead 90 includes a linear array of ultrasonic transducers aligned parallel to the y axis. The scanhead 90 transmits ultrasonic pulses in the directions of the parallel lines 96, which are preferably perpendicular to the x'-y' plane and parallel to the z'-y' plane. The array of transducers in scanhead 90 probe the underlying tissue lying (approximately) on lines 96 by detecting returns of the ultrasonic pulses caused by acoustic impedance discontinuities or reflecting surfaces within the tissue. The delay time between transmitting a pulse and receiving an return is indicative of the depth of the discontinuity or surface which caused the return. A characteristic such as magnitude, phase, or frequency of the returns is digitized and is plotted against the depth (z' axis) information and the information from the multiple transducers (dispersed in the y' direction) is assembled to construct an array representing a cross-sectional view of the tissue in a slice 98 parallel to the y-z plane and lying under scanhead 90.

Multiple slices can be scanned either by providing multiple scanheads, a two-dimensional scanhead array, or by moving the scanhead across the breast, for example in the x' direction in FIG. 4. The planes of only a few of the multiple slices, specifically slices 98, 100, and 102, are shown. In practice a large number of slices is desirable, for better resolution. A complete set of such slices is preferably scanned to form a three dimensional information set for at least some region of interest (ROI) chosen from the breast, which is preferably stored in a data structure (such as a three-dimensional array) to represent a three-dimensional image.

Ultrasonographic equipment is available commercially which can be used as the ultrasonographic imaging system 20 described above. A two-dimensional array of ultrasonographic data is usable by the invention, but with a diminished amount of useful information in the resulting display.

Figure 5A:
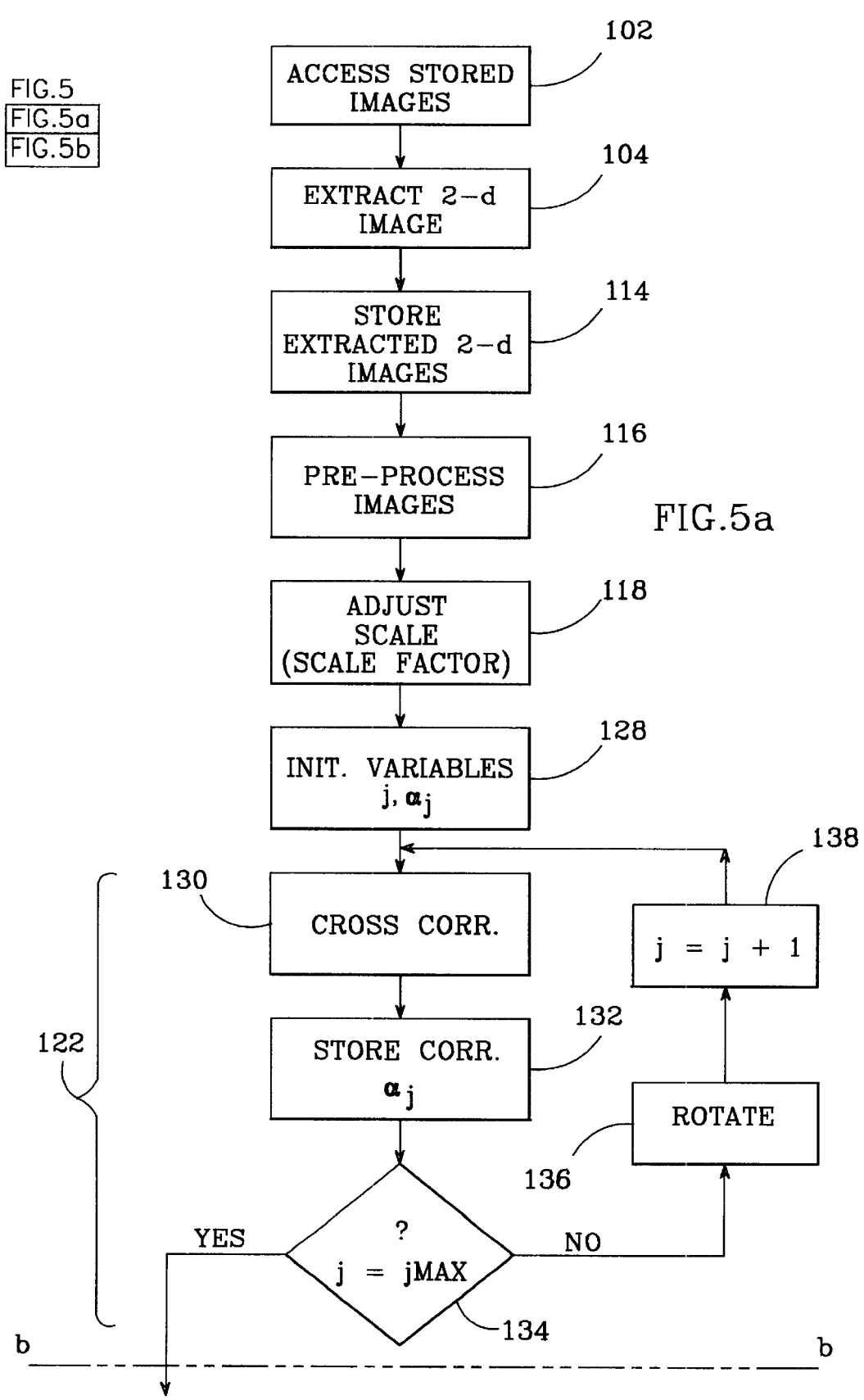
FIG. 5a is a flow chart showing the initial steps of a method of registering the pre-biopsy with the post-biopsy images, suitable for use in the registration step of FIG. 2.
Figure 5B:
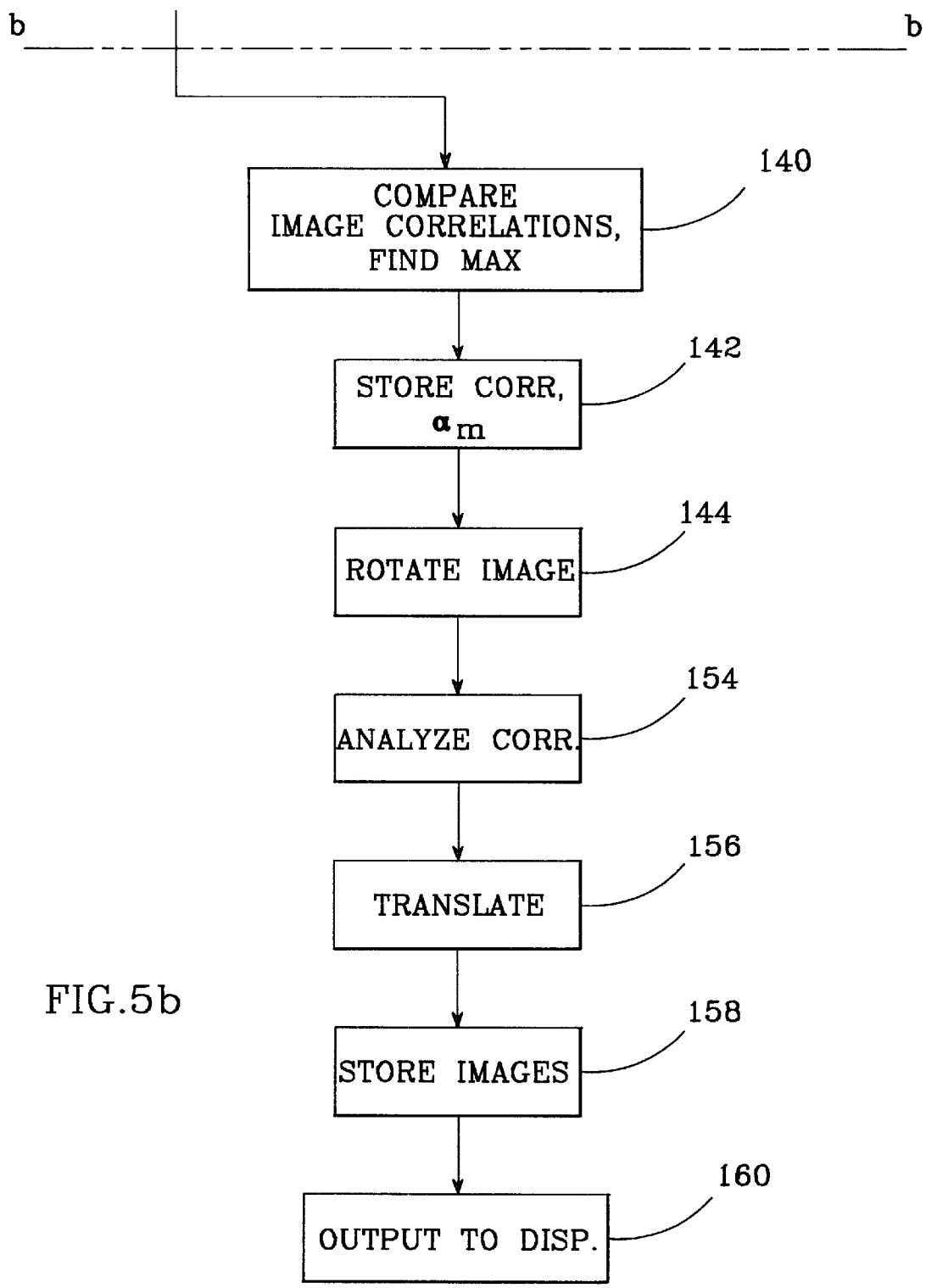
FIG. 5b is a flow chart continuing from FIG. 5a, showing the further steps in the method.

Keeping in mind the exemplary coordinate system of FIG. 3, a method suitable for registering the pre-biopsy and post-biopsy images (step 64) is shown in the flow chart of FIG. 5a (and continued on FIG. 5b). By this procedure the image processor 24 determines the proper coordinate transformations of scale, position, and rotation which will align the pre-biopsy and post-biopsy images. The image processor 24 accesses (step 102) the stored ultrasound images from ultrasonographic imaging system 20 and extracts (step 104) a two-dimensional representation preferably by projecting or "collapsing" the three-dimensional ultrasound data onto a single plane. One method of doing this is by "cumulative projection": a projection of the three-dimensional data set onto a two-dimensional plane by summing the data entries along vectors which are perpendicular to the projection plane. One such vector, vector 106, is indicated on FIG. 4 for illustration. The density values associated with the voxels (three dimensional discrete volume cells) such as voxel 110 are summed along the vector 106. The summation of those density values yields a scalar value which indicates the sum of the tissue densities along that vector. This scalar value is associated with the pixel 112 at the intersection of the vector 106 with the x-y plane. Repeating this summation for multiple parallel vectors results in a set of values which defines the projection of the three-dimensional sonographic imagery onto the x-y plane. This projection is preferably applied to both the pre-biopsy and post-biopsy imagery. Thus, returning to FIG. 5a, both three-dimensional data sets are projected onto respective two-dimensional images and stored (step 114).

The projected images are optionally further pre-processed (step 116). Pre-processing 116 can include any of a variety of known image processing techniques including (without limitation) contrast modification, smoothing, geometric transformation, thresholding or the selection of a region of interest. Depending on the type of optical correlator 30 used, as discussed in detail below, this step may also include two-dimensional Fourier transformation of the digitized x-ray image to prepare it for subsequent optical correlation in a Vanderlugt optical correlator.

Next the image processor 24 adjusts (step 118) the relative scale of the two images so that they at better correspond in scale. This can be done by various methods. For example, one method is to match the total area of the cross section of the breast area between the outer outline and the chest wall in both images. In this method, the images should preferably first be processed to remove low contrast features, leaving only the easily visible outline of the breast and the chest wall. The area between these features in the two dimensional images is then measured, for example by numerical integration by the image processor 24. The area should correspond in both images. If the areas do not correspond, it is possible that the degree of compression has changed, which can compress or expand the breast. A scaling correction factor is then preferably applied in step 118 to correct as closely as possible. On the other hand, it is possible in many cases to maintain a relatively constant compression. In such cases, little or no re-scaling is necessary.

After scale correction, the image processor 24 determines the rotation and translation necessary to align the images, preferably by interactively performing the steps grouped within the instruction loop 122 in FIG. 5a. First, two variables are initialized (step 128): a counter j to control execution of an instruction loop, and an associated rotation angle $\alpha_j$. Next, a cross-correlation of the dual images is computed (step 130). Preferably this step is accomplished by using the optical correlator 30 to perform the actual correlation computation, under control of the image processor 24. (The details of the optical correlator are discussed below, in connection with FIGS. 5 and 6) The cross-correlation (step 130) produces a two-dimensional correlation output image indicating the degree of image cross-correlation, which is stored (step 132) along with the associated rotation angle $\alpha_j$. The image processor then checks (step 134) the counter variable to discover whether it has completed a prescribed number of iterations of the instruction loop 122.

Next, if the counter variable j has not reached jmax, the image processor 24 continues and rotates (step 136) one of the dual images relative to the other by some angular increment, for example by rotating the pre-biopsy image one degree about an axis centered in the frame and parallel to the z axis. The counter is incremented (step 138) and the procedure loops back to step 130 to perform another cross-correlation, this time with the images rotated incrementally. The procedure is repeated until some number (jmax) of differently rotated correlations has been performed. The parameter jmax should be chosen to be large enough so that the range of the associated angle $\alpha_j$ encompasses the anticipated maximum possible range of rotation. For breast examination in the geometry shown in FIGS. 3 and 4, a range of less than 10 degrees is adequate in most cases.

The rotations applied in step 136 are not limited to rotations about a single axis, but can include rotations about multiple independent axes (or, equivalently rotations about an axis obliquely oriented with respect to the orthogonal axes shown). This allows the correction for an oblique viewing angle of one image with respect to the viewing angle of the other.

After the counter j reaches jmax the image processor 24 exits the instruction loop 122. The procedure continues as diagramed in FIG. 5b. The correlation output images previously stored in the various iterations of step 132 are compared (step 140) with one another to find the correlation output image with the maximum correlation, and its associated angle of rotation $\alpha_j$. The value $\alpha_m$ (the rotation angle which produced maximum correlation) is stored (step 142) and either the pre-biopsy or the post-biopsy image is rotated (step 144) by $\alpha_m$ to bring it into the same orientation as its counterpart.

Figure 6C:
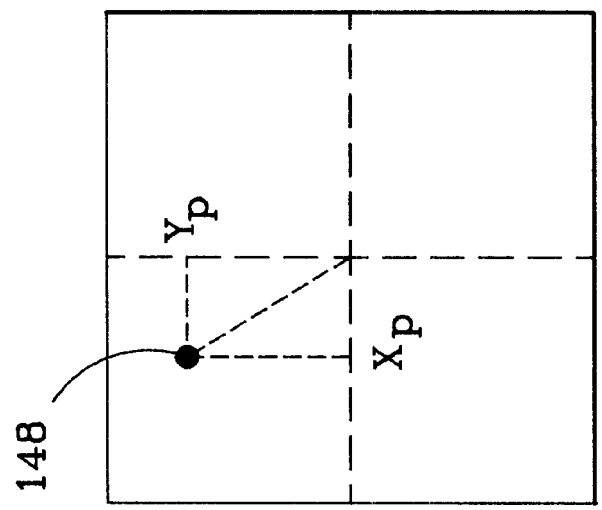
FIGS. 6a, 6b, and 6c, show simplified examples of an input image, a filter template, and a resulting correlation output image, respectively, in an example of a cross-correlation operation which discovers positional offset of correlated images.
Figure 6B:
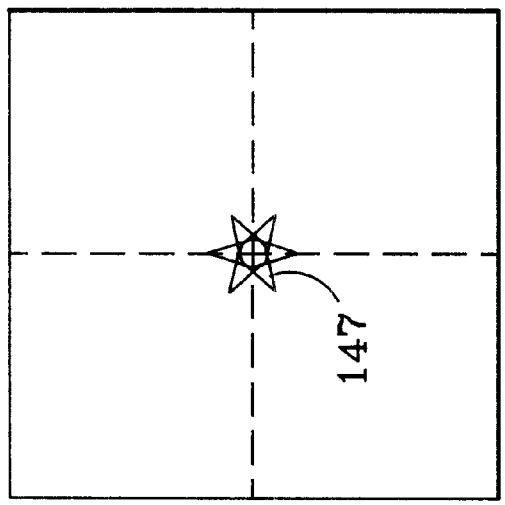
Figure 6A:
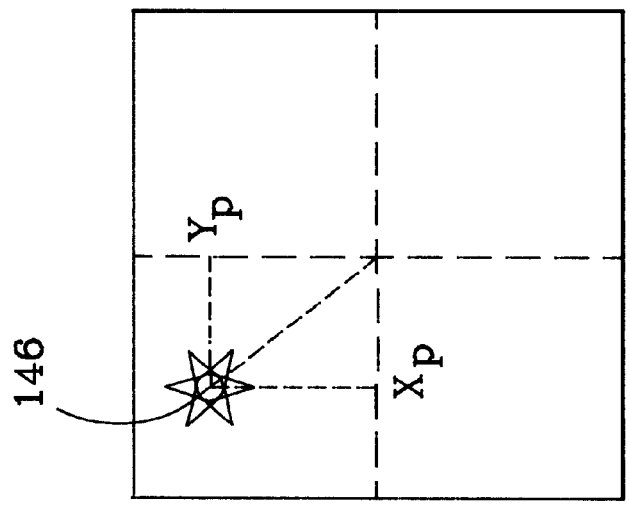

It should be understood that in addition to discovering the correct scale and rotation angles, the cross-correlation (step 130) in the above described procedure produces an output image which reveals the correct translation (position shift) which best aligns the dual images. The translation information is contained in the result of the cross-correlation operation (preferably in two-dimensions) defined as:

$$H(x,y)=g(x,y)*f(x,y)=\int\int f(\alpha,\beta)g(x-\alpha,y-\beta)d\alpha d\beta \quad (1)$$

Where f and g are functions of two variables (images), x and y are the spatial variables of the two-dimensional images, $\alpha$, and $\beta$ are dummy variables of integration, H is the cross-correlation of functions f and g, and the range of integration is across the entire image. If f and g differ only by a positional offset in x and y, H(x,y) will have a sharp peak at a position $x_p,y_p$ which is displaced from a central, correlation alignment position (typically defined as x=0, y=0) by a displacement corresponding to the offset between f and g. This well known result has been used to recognize and locate features of initially unknown locations in a field by reference to a template. See, for example, Russ, John C., *The Image Processing Handbook* (CRC Press, 1992), pp. 218–24. A simplified example is shown in FIGS. 6a–6c. The input image, a star 146 at an offset position shown in FIG. 6a, is correlated with a filter derived from the centered star-shaped template 147 shown in FIG. 6b. The resulting correlation output shown in FIG. 6c has a peak 148 at a position $x_p,y_p$ corresponding to the offset between the input image and the filter template. To align the images with a correlation peak at position $x_p,y_p$ it is sufficient merely to translate one of the images by a displacement equal to the offset $x_p,y_p$.

Returning to FIG. 5b, the image processor 24 next analyzes (step 154) the correlation output image to locate the positional offset of the correlation peak from an aligned correlation position, then translates (step 156) one image relative to the other as necessary to better align the images. After finding the optimal combination of rotations, scalings and translations to align the pre-biopsy and post-biopsy images, the image processor 24 preferably stores (step 158) the transformed images and the transformation parameters in its associated memory and preferably outputs (step 160) the transformed images to a display device 34. The visual output can be displayed in various forms, and various display formats can be used to allow the simultaneous display of both data sets in proper juxtaposition. For example, overlays, color coding, projection onto various planes, topographic quasi-three-dimensional display formats could be used, in various combinations.

Figure 7:
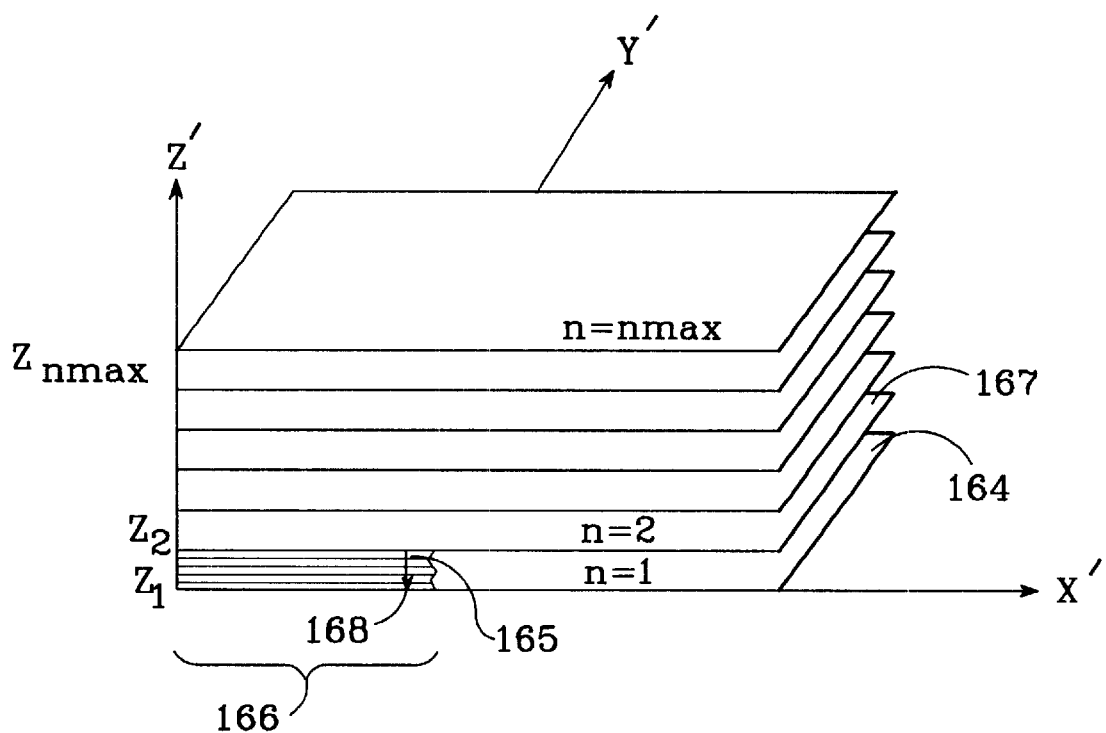
FIG. 7 is a perspective view of an arrangement of planar slices of a breast which can be selected for image processing of three-dimensional breast images by the invention.

In one embodiment the invention utilizes additional three-dimensional information about the subject body by further correlating the images in order to align the z direction (depth). To accomplish this, the ultrasonographic imagery is first partitioned by image processor 24 into conveniently defined slices, for example slice 164 as shown in FIG. 7. Each slice includes one or more layers of the three dimensional ultrasonographic image data. The slices are defined and calculated by image processor 24, for example by summing data points along vertical vectors such as 165, to collapse multiple thin layers into a thicker slice (a "partial cumulative projection"). In FIG. 7, for example, multiple thin layers 166 of ultrasonographic imagery (shown only partially to clarify FIG. 7) might lie between bottom slice 164 and the immediately overlying slice 167. The partial cumulative projection is taken point-by-point, by summing the ultrasonographic image values at points along vectors such as vector 165, and accumulating the result to the point 168 where vector 165 intersects the slice 164. The accumulated data values at each defined point on slice 164 collectively define the slice.

In a typical application, slices of 5 millimeters or less in thickness are suitable. Although planar slices are convenient for purposes of illustration, in some applications the slices might usefully be taken along non-planar contours. Such slices are also within the scope of the invention. Thinner slices are desirable for better depth definition with thin features.

To best align the pre-and post-biopsy images, corresponding slices in each are individually correlated to find their best registration, for example by the method described above. In one variation of this technique, the slices are defined parallel to the X'Y' plane. In another variation, the slices are defined in another plane (the slice under the scanhead, parallel to the Z'Y' plane, for example) and registered by the above described method, then reassembled. By registering each slice, the three-dimensional imagery can be aligned to account for variations in shear or torque between the pre-and post-biopsy procedures, as might be caused by deformation of the breast under varying pressure.

Figure 8:
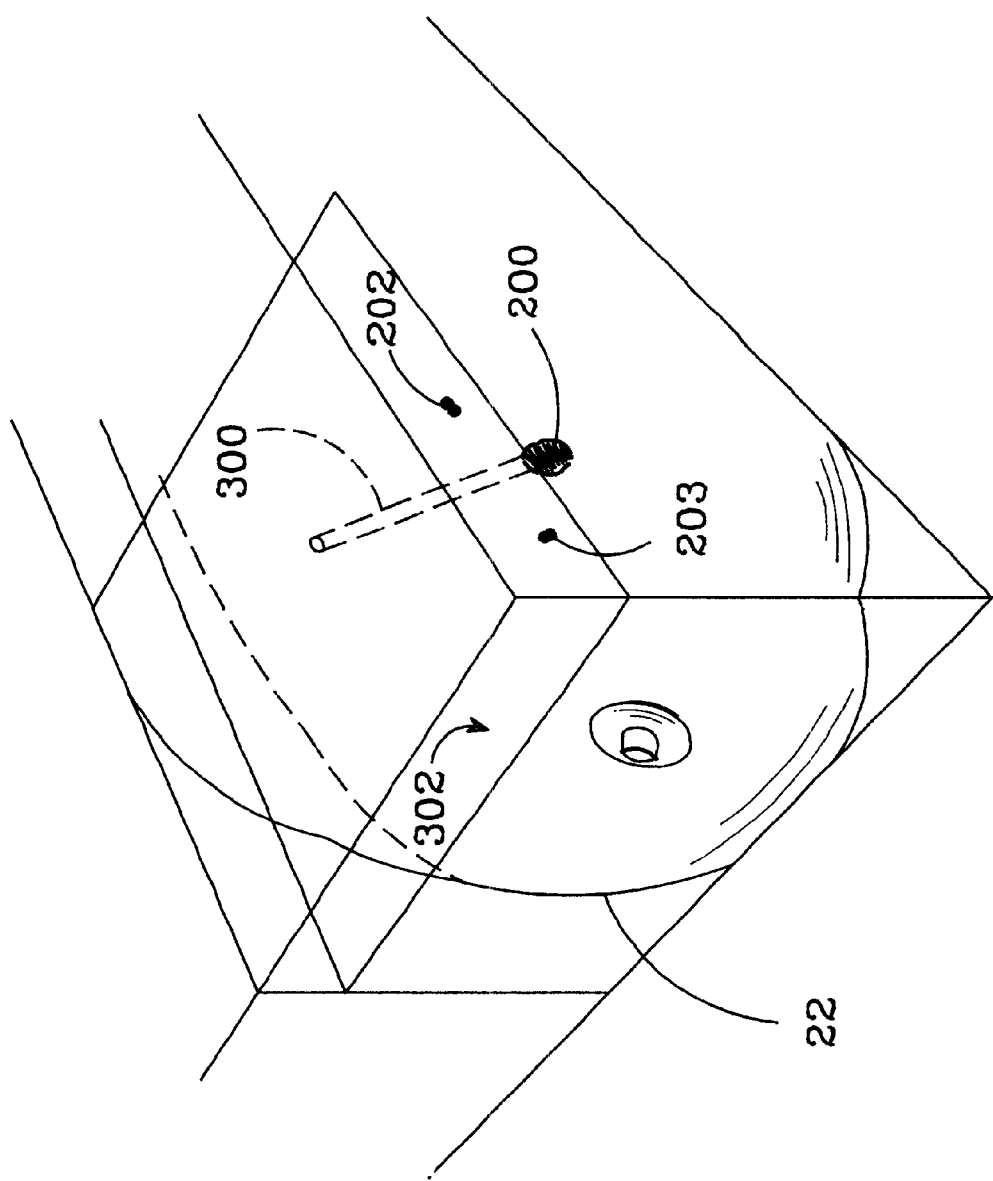
FIG. 8 is a perspective diagram representing a typical visual display of a composite image created by the invention to document a needle biopsy.

After the pre-biopsy and post-biopsy images are adjusted to best register them, they can be either combined by adding, voxel-by-voxel, or compared by subtracting, voxel-by-voxel. Differences between the pre-biopsy and post-biopsy are easily highlighted by changing the color at voxels which show high variation between the dual biopsy images. FIG. 8 shows an example of one method of display of a typical combined image. The outline of the breast 22 is shown, with biopsy region 200 (a suspect lesion simplified for illustration) as revealed by ultrasonography. Other visible regions of density 202 and 203 are shown, which would suitably be displayed in a neutral color or grey scale. A trajector of a biopsy needle 300 (or equivalent instrument) would preferably be color coded for display(for example, green), while the region 200 where tissue was removed would preferably be coded in a different color (for example, pink). This three dimensional image, easily digitized and archived on computer readable media, provides easily readable documentation of the biopsy procedure, and can be retrieved for evidence that the intended target tissue was indeed sampled. The image processor can also extract slices such as that cut by imaginary plane 302, and display the slice as a two-dimensional section for detailed inspection. Preferably, the processor is programmed to respond to user input so that any slice can be selected for display, or the user can sweep through multiple slices to view details of interest.

In the procedures depicted in FIGS. 5a and 5b it is highly preferable that the correlation operations be carried out by an optical correlator. In the preferred embodiment, the image processor 24 electronically writes the dual images to the optical correlator 30. The optical correlator 30 preferably performs the correlation operations and returns a resulting correlation image to the image processor 24.

Optical correlators use wave optics to correlate images in two dimensions by first performing essentially a two-dimensional spatial Fourier transform on a two-dimensional source image. This method takes advantage of a well known mathematical property of the Fourier transform: many operations including correlation are more easily calculated in the Fourier transform domain than the original spatial domain. Specifically, a two-dimensional correlation operation is defined by equation 1 (above), where f(x,y) and g(x,y) are the two-dimensional functions or images to be cross-correlated, and $\alpha$ and $\beta$ are dummy variables of integration. This operation can be performed digitally for each point x,y by numerical techniques, but a very large number of calculations are required even for one image correlation. Performing such an operation digitally is very time consuming and requires inconvenient lengths of time on any but the fastest digital computers.

Unlike a conventional digital computer, an optical correlator can very rapidly perform a correlation operation, correlating a source image with a filter image by (1) optically Fourier transforming a source image, (2) comparing the source and filter image in the Fourier transform domain, and then (3) performing an inverse Fourier transformation to produce the correlation pattern in a spatial representation. An optical correlator can accomplish these operations much faster that a digital computer because the optical Fourier transformation is executed as a simultaneous operation on all points of the source image, using inherent properties of wave optics to generate the Fourier transform in two dimensions. The speed of the device is limited for practical purposes only by the available read and write speed of the data transfer to the correlator; the actual optical processes occur in fractions of a nanosecond in typical optical correlators.

The principles of the optical correlator are known, and have been described for example in the U.S. Pat. No. 5,311,359, to Lucas et al. Compact optical correlators suitable for use in the present invention are commercially available from Litton Data Systems, Inc., in Agoura Hills, Calif., as well as from other sources. Alternate types of optical correlators such as the Joint Transform Correlators described in U.S. Pat. No. 5,650,855 to Kirsch et al., U.S. Pat. No. 5,216,541 to Taksue et al. or U.S. Pat. No. 5,438,632 to Horner, may also be employed with the invention.

Figure 9:
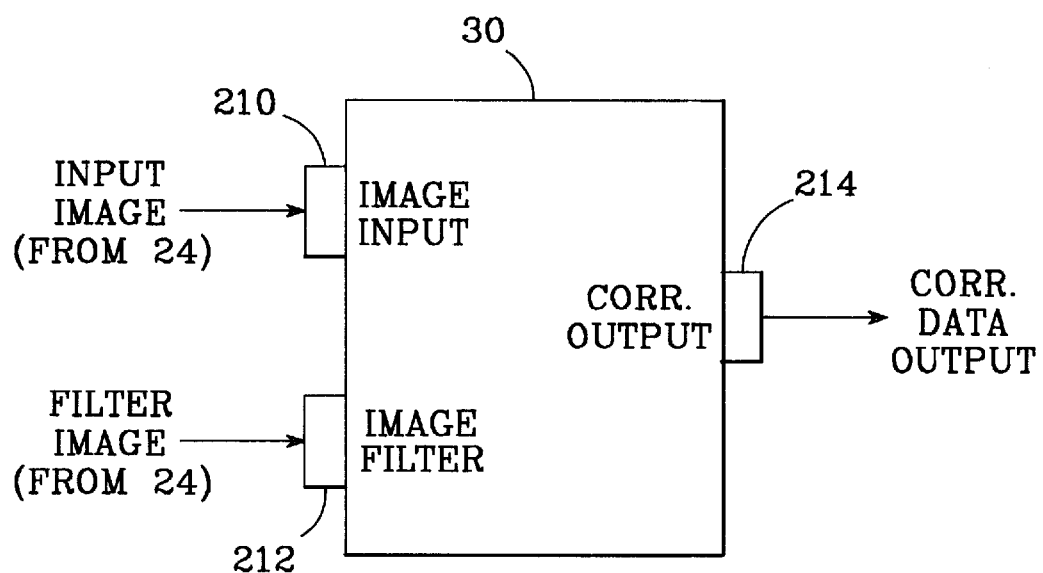
FIG. 9 is a symbolic diagram of an optical correlator, optionally used in accordance with a variation of the invention for rapidly performing two-dimensional correlation operations, thereby aiding in registering the pre-biopsy and post-biopsy images.

For purposes of describing the present invention, the optical correlator 30 may be considered functionally as an electro-optical device having three (electronic) ports, as shown in FIG. 9. The three ports include: (1) an image input port 210 for receiving an electronic signal encoding an input image for correlation; (2) a filter input port 212 for receiving a second electronic signal encoding a second image or "filter" for correlation; and (3) an output port 214, typically from a charge coupled device (CCD) imager, which converts the correlation image into electrical form for output. In addition the device requires a source (not shown) of preferably coherent electromagnetic radiation, typically a laser, which provides the medium used for computation.

Both the image input port 210 and the filter input port 212 are realized as two-dimensional spatial light modulators (SLMs) organized as two-dimensional image matrices, with addressable image pixels (typically arranged in the familiar row and column pattern). Accordingly, the input image must be formatted (suitably by image processor 24) to fit the matrix; and each pixel of data should preferably be addressed, under control of the image processor 24, to the spatially corresponding pixel on the SLM. For example, in one embodiment of the invention, the image input port and the filter input port are realized as 256×256 pixilated matrices. Accordingly, in this embodiment the image processor 24, as part of pre-processing step 116 (in FIG. 5a), maps an ultrasonographic image onto a 256×256 matrix for output to the optical correlator 30. In a typical embodiment of the invention a Vanderlugt type optical correlator is used. In such a correlator the "filter" image must be pre-processed by two-dimensional Fourier transformation. In such an embodiment the image written to the filter port is preferably Fourier transformed by image processor 24 (for example in pre-processing step 116), to provide a frequency domain pattern. In an alternate embodiment, a joint transform correlator may be used as optical correlator 30. This eliminates the need for the digital Fourier transformation of the filter image, as the transformation is optically performed by the joint transform correlator.

Note that in conventional, practical high speed optical correlators, the SLMs and the photodetector matrix consist of discrete pixels rather than a continuously modulatable surface. Thus, the Fourier transformation and correlation operations can only approximate the discrete cross-correlation (given by equation 1, above). However, the approximation obtained is sufficient for image processing for most applications.

When the input the filter images have been written to the input and filter ports 210 and 212, the optical correlator produces an output image which is a two dimensional output correlation pattern having an optical peak or peaks (bright spot) at the position of greatest correlation between the collapsed sonographic image and the radiographic image. The degree of correlation is indicated by the intensity of the output signal. The position of the output peak on the two-dimensional matrix of the correlator output CCD indicates the translations or shifts of the images relative to one another. The output image is read from the output photodetector (CCD) 214 by the image processor 24 in the conventional manner, typically by shifting the CCD voltage values out sequentially in rows (or columns) and then digitizing the output levels.

Although the invention is described in terms of linear transformations of the coordinates, such as translation, rotation, and scale multiplication, the invention is not limited to linear transformations. Non-linear transformations of coordinate systems may be useful in some applications. For example, the ultrasonographic information may be obtained with the breast differently deformed, as by a change of position of the subject, or by instrument pressure. By applying a mathematical transformation, which may in general be non-linear, a better mapping of the deformed subject breast onto the original subject breast can be obtained. Similarly, some scanning techniques may involve curvilinear, non-cartesian coordinate systems which would be treated with non-linear transformations.

While illustrative embodiments of the invention are described above, it will be evident to one skilled in the art that numerous variations, modifications and additional embodiments may be made without departing from the invention. For example, the construction of the ultrasound imaging system or the geometries and coordinate systems employed may be varied. Various means of data storage, transmission, or processing may be employed. The resolution or type of image that is sent from the image processor to the optical correlator could also be altered. Three-dimensional cross-correlations are also possible (but computationally complex). To the extent that such operations can be decomposed into multiple planar operations, the use of the optical correlator as described above could greatly accelerate computations. Accordingly, it is intended that the invention be limited only in terms of the appended claims.

We claim:

1. A method of visually documenting the in-vivo location from which a biopsy specimen has been extracted, comprising the steps of:

(a) before a biopsy is taken, obtaining a first image of a region of tissue;

(b) after a biopsy of said region, obtaining a second image of said region of tissue; and (c) creating from said first and second images a composite image which visually emphasizes differences between said first and second images, thereby visually representing in-vivo location from which the biopsy tissue was sampled.

2. The method of claim 1, further comprising the step of recording said composite image for archiving.

3. The method of claim 2, wherein said step of recording comprises storing said composite image on a computer readable medium.

4. The method of claim 2, wherein said step of recording comprises printing an image based upon said composite image.

5. The method of claim 1, wherein at least one of said first and second images is a three dimensional image model.

6. The method of claim 1, wherein said step of creating a composite image comprises:

spatially adjusting at least one of said first and second images to spatially register said first and second images.

7. The method of claim 6, wherein said step of spatially adjusting at least one of said first and second images comprises:

determining a coordinate transformation which produces a pre-determined degree of correlation between said first and second images; and applying said coordinate transformation to at least one of said first and second images, to align said images.

8. The method of claim 7, wherein said coordinate transformation is determined by:

(a) applying a plurality of coordinate transformations to one of said first and second images, to obtain a plurality of corresponding adjusted images;

(b) cross-correlating said adjusted images with one of said first and second images, to produce a correlation output; and (c) selecting a coordinate transformation which produces a defined correlation output from its corresponding adjusted image.

9. The method of claim 1, wherein said composite image visually emphasizes image differences by representing various regions of said composite image in synthetic colors, based upon image differences between the pre-biopsy image and the post-biopsy image.

10. The method of claim 1, wherein said composite image visually emphasizes image differences by tagging regions in the composite image with synthetic icons to indicate probably biopsy tissue sample locations.

11. A method of creating a displayable composite mammographic image from a plurality of raw mammographic images, corresponding to pre-biopsy and post-biopsy mammographic images, comprising the steps of:

(a) obtaining a pre-biopsy image of a region of tissue;

(b) obtaining a post-biopsy image of substantially the same region of tissue;

(c) deriving a difference image which represents changes between said pre-biopsy image and said post-biopsy image; and (d) combining at least one of said pre-biopsy and said post-biopsy images with said difference image, to produce a composite image.

12. The method of claim 11, further comprising the step of recording said composite image for archiving.

13. The method of claim 12, wherein said step of recording comprises storing said composite image on a computer readable medium.

14. The method of claim 12, wherein said step of recording comprises printing an image based upon said composite image.

15. The method of claim 11, wherein at least one of said pre-biopsy and post-biopsy images is a three dimensional image model.

16. The method of claim 11, wherein said step of creating a composite image comprises:

spatially adjusting at least on of said pre-biopsy and post-biopsy images to aid in registering said images.

17. The method of claim 16, wherein said step of spatially adjusting at least one of said pre-biopsy and post-biopsy images comprises:

determining a coordinate transformation which produces a desired degree of correlation between said pre-biopsy and post-biopsy images; and applying said coordinate transformation to at least one of said pre-biopsy and post-biopsy images, to align said images.

18. The method of claim 17, wherein said coordinate transformation is determined by:

(a) applying a plurality of coordinate transformations to one of said pre-biopsy and post-biopsy images, to obtain a plurality of corresponding adjusted images;

(b) cross-correlating said adjusted images with one of said pre-biopsy and post-biopsy images, to produce a correlation output; and (c) selecting a coordinate transformation which produces a defined correlation output from its corresponding adjusted image.

19. The method of claim 11, comprising the further step of inserting a visual icon into the composite image to mark a region of biopsied tissue.

20. A system for enhancing imagery of bodily tissues by relating pre-biopsy and post-biopsy images, comprising:

an image processor, programmed to: (a) receive said pre-biopsy and post-biopsy images, (b) register the pre-biopsy and post-biopsy images by controlling an optical correlator to find a position of correlation between said pre-biopsy and post-biopsy images, and (c) derive a composite image from the pre-biopsy and post-biopsy images; and an optical correlator coupled to said image processor and arranged to correlate said pre-biopsy and post-biopsy images, and to output to said image processor a cross correlation image which is indicative of the position of correlation of the processed images.

21. The system of claim 20, wherein said image processor is further programmed to compute differences between said pre-biopsy and said post-biopsy images and to emphasize said differences in said composite image.

22. The system of claim 20, further comprising a visual display, coupled to said image processor and receiving from said image processor said composite image, to permit a user to view said composite image.

23. The system of claim 20, further comprising an ultrasonographic imaging system, arranged to communicate ultrasonographic image data to said image processor to provide at least one of pre-biopsy and post-biopsy images.

* * * * *